United States Patent [19]

Broka

[11] Patent Number: 5,721,267
[45] Date of Patent: Feb. 24, 1998

[54] CHEMOTHERAPEUTIC PYRROLOCARBAZOLE DERIVATIVES

[75] Inventor: Chris Allen Broka, Foster City, Calif.

[73] Assignee: Syntex (U.S.A.) Inc., Palo Alto, Calif.

[21] Appl. No.: 787,594

[22] Filed: Jan. 22, 1997

Related U.S. Application Data

[63] Continuation of Ser. No. 286,043, Aug. 4, 1994, abandoned.

[51] Int. Cl.$^6$ .......................... C07C 487/04; A61K 31/40
[52] U.S. Cl. .......................... 514/410; 514/339; 548/423; 546/276.7
[58] Field of Search ............................... 548/423; 514/410

[56] References Cited

U.S. PATENT DOCUMENTS

| | | | |
|---|---|---|---|
| 4,912,107 | 3/1990 | Kleinschroth et al. | 514/232.5 |
| 4,999,369 | 3/1991 | Bair | 514/410 |
| 5,057,614 | 10/1991 | Davis et al. | 548/466 |
| 5,166,204 | 11/1992 | Nagai et al. | 514/232.8 |

FOREIGN PATENT DOCUMENTS

| | | |
|---|---|---|
| 2010636 | 3/1993 | Canada . |
| 0 269 025 | 6/1988 | European Pat. Off. . |
| 0 362 695 | 4/1990 | European Pat. Off. . |
| 0 624 586 | 11/1994 | European Pat. Off. . |
| 4 034 687 | 5/1991 | Germany . |
| 91/13071 | 9/1991 | WIPO . |
| 93/24491 | 12/1993 | WIPO . |
| 94/27982 | 12/1994 | WIPO . |

OTHER PUBLICATIONS

Toullec et al., "The bisindolylmaleimide GF 109203X is a potent and selective inhibitor of protein kinase C", J. Biol. Chem., 266(24), 15771–15781 (1991).
Bit et al., "Inhibitors of protein kinase C. 3. Potent and highly selective bisindolylmaleimides by conformatiion restriction", J. Med. Chem., 36, 21–29 (1993).
Davis et al., "Inhibitors of protein kinase C. 1. 2,3–Bisarylmaleimides" J. Med. Chem., 35, 177–184 (1992).
Davis et al., "A mild conversion of maleic anhydrides into maleimides", Tetrahedron Lett., 31(36), 5201–5204 (1990).
Davis et al., "A convenient synthesis of bisindolyl–and indolylaryl–maleic anhydrides", Tetrahedron Lett., 31(16), 2353–2356 (1990).
Davis et al., "Potent selective inhibitors of protein kinase C", FEBS Lett., 259(1), 61–63 (1989).
Eenkhorn et al., "The Wittig reaction of indole–2–methyltriphenylphosphonium iodide . . . ", Can. J. Chem., 51(5), 792–810 (1973).
Schröder et al., Arzneimittelchemie I, Georg Thieme Verlag, Stuttgart, Germany, 1976, pp. 24–38 cited.
Eitel et al., "New regio–and stereo–controlled reactions of 2–vinylindoles . . . ", Heterocycles, 27(10), 2353–2362 (1988) [see also Chem. Abstracts, 111(9), 77796g (1989).
Winograd, B. Oxford Textbook of Oncology, vol. 1, ed. by Peckham, M. et al. (Oxford University Press, Oxford), p. 486 (1995).
Cleton, F.J. Oxford Textbook of Oncology, vol. 1, ed. by Peckham, M. et al. (Oxford University Press, Oxford), pp. 445–453 (1995).
Workman, P. et al. Oxford Textbook of Oncology, vol. 1, ed. by Peckham, M. et al. (Oxford University Press, Oxford), p. 506 (1995).
Crilley, P.A. et al. Basic Pharmacology in Medicine, ed. by Dipalma, J.R. et al. (Medical Surveillance Inc., West Chester), pp. 659–661(1994).
Mayer, R.J. Harrison's Principles of Internal Medicine, vol. 2, ed. by Isselbacher, K.J. et al. (McGraw–Hill, N.Y.), pp. 1382–1386 and 1532–1535(1994).
Hochberg, F. et al. Harrison's Principles of Internal Medicine, vol. 2, ed. by Isselbacher, K.J. et al. (McGraw–Hill, N.Y.), pp. 2256–2269 (1994).
Colucci, W.S. et al. Harrison's Principles of Internal Medicine, vol. 1, ed. by Isselbacher, K.J. et al. (McGraw–Hill, N.Y.), pp. 1101–1105 (1994).
Blobe, G.C. et al. Cancer and Metastasis Reviews, vol. 13, p. 411, the abstract only (1994).

Primary Examiner—Mukund J. Shah
Assistant Examiner—King Lit Wong
Attorney, Agent, or Firm—Heller Ehrman White & McAuliffe

[57] ABSTRACT

Compounds represented by the Formula I:

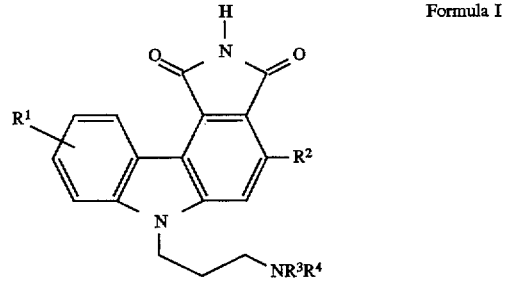

Formula I wherein:
 $R^1$ is hydrogen or lower alkyl;
 $R^2$ is heteroaryl; and
 $R^3$ and $R^4$ are independently hydrogen or lower alkyl; and the pharmaceutically acceptable salts thereof, are useful as chemotherapeutic agents.

5 Claims, No Drawings

CHEMOTHERAPEUTIC PYRROLOCARBAZOLE DERIVATIVES

CROSS-REFERENCE TO RELATED APPLICATION

This application is a continuation of application Ser. No. 08/286,043, filed Aug. 4, 1994, now abandoned.

FIELD OF THE INVENTION

The present invention relates to pyrrolocarbazole derivatives. The invention is also directed to formulations thereof and methods for treating malignant diseases.

BACKGROUND INFORMATION

It has long been sought to provide chemotherapeutic agents useful for treating various malignant diseases. The pyrrolocarbazole derivatives of the present invention are protein kinase C inhibitors useful as chemotherapeutic agents. Other pyrrolocarbazole derivatives and related compounds/protein kinase C inhibitors have been described in the literature as having various activities, such as the treatment of inflammatory, immunological, bronchopulmonary, cadiovascular, malignant, and allergic disorders. See, e.g., U.S. Pat. Nos. 4,912,107, 5,057,614, and 5,166,204; EPO 0-328-026-A1, 0-384-349-A1; and PCT WO 91/13070 and 91/13071. See also, e.g., the following publications of Davis, et al.: Febs Letters, Vol. 259, No. 1, 61–63 (1989); Tetrahedron Letters, Vol. 31, No. 16, 2353–2356 (1990); Tetrahedron Letters, Vol. 31, No. 36, 5201–5204 (1990); and J. Med. Chem., Vol. 35, 177–184 (1992); and Bit, et al., J. Med. Chem., Vol. 36, 21–29 (1993).

SUMMARY OF THE INVENTION

One aspect of the present invention concerns pyrrolocarbazole derivatives of Formula I:

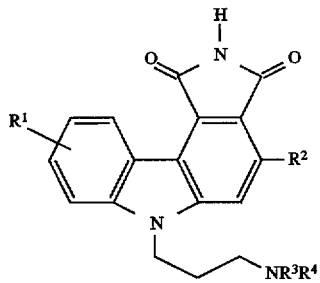

Formula I wherein
$R^1$ is hydrogen or lower alkyl;
$R^2$ is heteroaryl; and
$R^3$ and $R^4$ are independently hydrogen or lower alkyl; and the pharmaceutically acceptable salts thereof.

In a preferred aspect, the invention relates to certain compounds of Formula I, particularly including the compounds where $R^1$ is hydrogen and $R^2$ is thiophenyl.

In another aspect, the invention relates to a pharmaceutical composition containing a therpeutically effective amount of a compound of Formula I or a pharmaceutically acceptable salt thereof admixed with at least one pharmaceutically acceptable excipient.

In still another aspect, the invention relates to a method of treating malignant disorders, particularly small cell lung carcinoma, colon carcinoma, and renal and prostate tumors in a mammal, particularly in a human, by administering to a mammal in need of such treatment a therapeutically effective amount of a compound of Formula I or a pharmaceutically acceptable salt thereof.

DETAILED DESCRIPTION OF THE INVENTION

Definitions and General Parameters

The following definitions are set forth to illustrate and define the meaning and scope of the various terms used to describe the invention herein.

The term "lower alkyl" means a monoradical branched or unbranched saturated hydrocarbon chain containing 1 to 6 carbon atoms, such as methyl, ethyl, n-propyl, isopropyl, n-butyl, tert-butyl, n-pentyl, n-hexyl.

The term "heteroaryl" refers to a monovalent unsaturated aromatic carbocyclic radical having a single ring of 5 or 6 atoms, one of which is a hetero atom chosen from N, O, or S, for example thiophenyl, furanyl, pyrrolyl, and pyridyl, which can optionally be mono-, di- or tri-substituted independently with hydroxy, lower alkyl, lower alkoxy, chloro, fluoro, trifluoromethyl and/or cyano.

"Optional" or "optionally" means that the subsequently described event or circumstance may or may not occur, and that the description includes instances where said event or circumstance occurs and instances in which it does not.

A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

Nomenclature

The compounds of Formula I are named and numbered as described below:

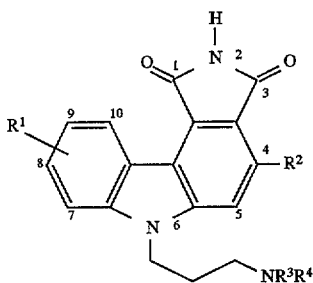

For example, the compound of Formula I where $R^1$ is hydrogen, $R^2$ is 3-thiophenyl, $R^3$ is hydrogen and $R^4$ is methyl, a preferred compound of the invention, is named: 1,3-dioxo-6-(3-methylaminopropyl)-1,2,3,6-tetrahydro-4-(thiophen-3-yl)-pyrrolo [3,4-c]carbazole.

Other examples are shown below:

| No. | $R^1$ | $R^2$ | $R^3$ | $R^4$ |
|---|---|---|---|---|
| 1 | H | 3-thiophenyl | H | ethyl |
| 2 | 8-methyl | 2-thiophenyl | H | methyl |
| 3 | H | 3-furanyl | H | methyl |
| 4 | H | 3-pyrrolyl | methyl | methyl | are respectively named as follows:
1. 1,3-dioxo-6-(3-ethylaminopropyl)-1,2,3,6-tetrahydro-4-(thiophen-3-yl)-pyrrolo[3,4-c]carbazole. 2. 1,3-dioxo-8-methyl-6-(3-methylaminopropyl)-1,2,3,6-tetrahydro-4-(thiophen-2-yl)-pyrrolo[3,4-c]carbazole.
3. 1,3-dioxo-6-(3-methylaminopropyl)-1,2,3,6-tetrahydro-4-(furan-3-yl)-pyrrolo[3,4-c]carbazole.
4. 1,3-dioxo-6-(3-(dimethylamino)propyl)-1,2,3,6-tetrahydro-4-(pyrrol-3-yl)-pyrrolo[3,4-c]carbazole.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures.

Specific illustrations of suitable separation and isolation procedures can be had by reference to the examples hereinbelow. However, other equivalent separation or isolation procedures can, of course, also be used.

Synthesis of the Compounds of Formula I

The compounds of Formula I can be prepared by following the procedures described below with reference to Reaction Scheme 1. As used in the Reaction Schemes, the substituents, e.g., $R^1$, $R^2$, $R^3$, and $R^4$ have the same meaning as described in the Summary of the Invention, unless otherwise indicated.

Starting Materials

The optionally substituted N,N-di(lower alkyl) aminomethylindoles of Formula 1 are commercially available, or may be readily prepared by those skilled in the art using commonly employed synthetic methodology. For example, N,N-dimethylaminomethylindole is available from Aldrich Chemical Company, Milwaukee, Wis.

REACTION SCHEME 1

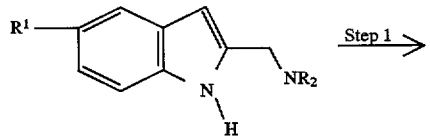

Formula 1

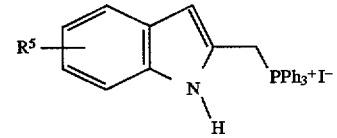

Formula 2 where R is lower alkyl;

Formula 2 $\xrightarrow[\text{Step 2}]{R^2CHO}$ 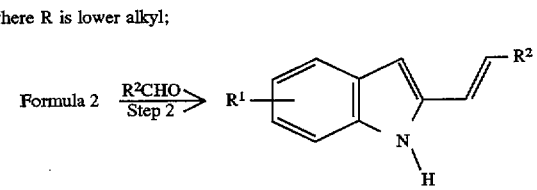

Formula 3

Formula 3 $\xrightarrow[\text{Step 3}]{}$ 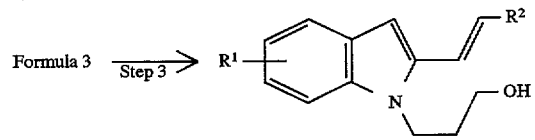

Formula 4

Formula 4 $\xrightarrow[\text{Step 4}]{}$ 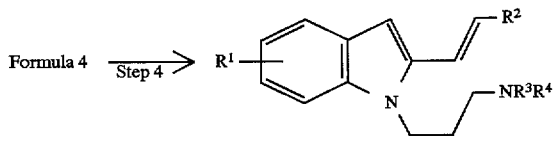

Formula 5

Formula 4 $\xrightarrow[\text{Step 4a}]{}$

-continued
REACTION SCHEME 1

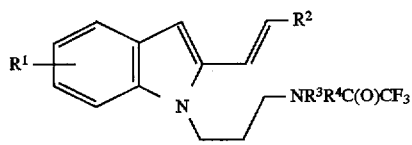

Formula 5a

Step 4a is only carried out if at least one of $R^3$ and $R^4$ is hydrogen;

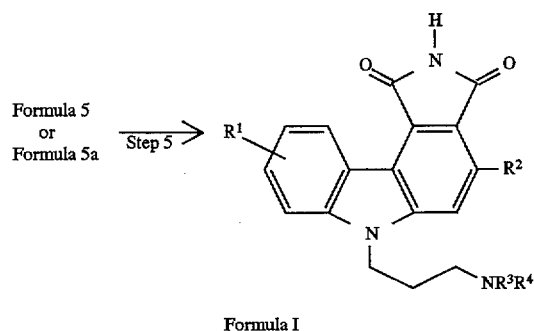

Preparation of Formula 2

As illustrated in Reaction Scheme 1, Step 1, an optionally substituted N,N-di(lower alkyl)aminomethylindole of Formula 1 is converted to an optionally substituted phosphonium salt of Formula 2 by the method disclosed in *Canadian J. Chem.*, Vol. 51, p 792 (1973).

The compound of Formula 1, preferably N,N-dimethylaminoethylindole, is dissolved in a protic solvent, preferably methanol, and reacted with an excess of methyl iodide at between 10° C. to 50° C. (preferably 25° C.) for 1 to 10 hours (preferably 3 hours). About 1 molar equivalent of triphenylphosphine in a polar solvent (preferably dimethylformamide) is then added to the product and the mixture maintained at 100°–150° C., preferably at reflux, for 6 to 24 hours, preferably 16 hours. When the reaction is substantially complete, the optionally substituted phosphonium salt of Formula 2 is isolated and purified by conventional means, preferably by crystallization.

Preparation of Formula 3

As illustrated in Reaction Scheme 1, Step 2, an optionally substituted phosphonium salt of Formula 2 is reacted with a heteroaryl aldehyde of Formula $R^2CHO$ in the presence of a base to give a vinylindole of Formula 3.

The optionally substituted phosphonium salt of Formula 2 is dissolved in a polar aprotic solvent (preferably DMSO) and reacted with an aldehyde of formula $R^2CHO$ in the presence of a hindered base (preferably 1,5-diazabicyclo[4.3.0]non-5-ene or 1,8-diazabicyclo[5.4.0]undec-7-ene). Reaction is carried out at 20°–100° C. (preferably 80° C.) for about 2 hours, followed by stirring at about 20° C. for 6–48 hours (preferably about 16 hours). When the reaction is substantially complete, the vinylindole of Formula 3 is isolated and purified by conventional means, preferably by silica gel chromatography or crystallization.

Preparation of Formula 4

As illustrated in Reaction Scheme 1, Step 3, a vinylindole of Formula 3 is reacted with 1-iodo-3-(t-butyl)diphenylsilyloxypropane, and deprotected to give an N-alkylated vinylindole of Formula 4.

The vinylindole of Formula 3 is dissolved in a polar aprotic solvent (preferably DMF or DMSO) and treated with an alkali metal hydride, for example potassium hydride or sodium hydride (preferably potassium hydride) at a temperature of 0°–50° C. (preferably 25° C.). After reacting for 5 minutes to 3 hours (preferably 15 minutes), 1-iodo-3-(t-butyl)diphenyl-silyloxypropane is added, and the reaction stirred at the same temperature for about 1–24 hours (preferably about 16 hours). When the reaction is substantially complete, the silyl protected compound is isolated and purified by conventional means, preferably by silica gel chromatography. The silyl group is removed by treatment with tetrabutylammonium fluoride or pyridine-hydrofluoric acid in tetrahydrofuran or dimethoxyethane at 20°–30° C. for between 1 and 12 h (preferably 2 hours). The N-alkylated vinylindole of Formula 4 is preferably purified by silica gel chromatography.

Preparation of Formula 5

As illustrated in Reaction Scheme 1, Step 4, the hydroxy group of a compound of Formula 4 in which both $R^3$ and $R^4$ are lower alkyl is converted to a vinyl amine of Formula 5.

The alcohol of Formula 4 is dissolved in methylene chloride or chloroform (preferably methylene chloride) and treated with a hindered base (for example 2,6-lutidine or 2,4,6-collidine, preferably 2,6-lutidine), followed by trifluoromethanesulfonic anhydride at between −10° C. to 20° C. (preferably 0° C.) for 15 minutes to 1 hour (preferably 30 minutes). The product is then reacted with an excess of amine of formula $R^3R^4NH$, where $R^3$ and $R^4$ are lower alkyl, at a temperature of 0°–40° C. (preferably 25° C.) for about 3 hours, followed by reaction at about 0° C. for 6–24 hours (preferably 12 hours). When the reaction is substantially complete, the amine of Formula 5 is isolated and either purified by conventional means, preferably silica gel chromatography, or used directly in step 5.

Preparation of Formula 5a

As illustrated in Reaction Scheme 1, Step 4a, the hydroxy group of a compound of Formula 4 in which at least one of $R^3$ and $R^4$ is hydrogen is converted to a protected vinyl amine of Formula 5a.

The alcohol of Formula 4 is dissolved in methylene chloride or chloroform (preferably methylene chloride) and treated with a hindered base (for example 2,6-lutidine or 2,4,6-collidine, preferably 2,6-lutidine), followed by trifluoromethanesulfonic anhydride at between −10° C. to 20° C. (preferably 0° C.) for 15 minutes to 1 hour (preferably 30 minutes). The product is then reacted with an excess of amine of formula $R^3R^4NH$, where at least one of $R^3$ and $R^4$ is hydrogen, at a temperature of 0°–40° C. (preferably 25° C.) for about 3 hours, followed by reaction at about 0° C. for 6–24 hours (preferably 12 hours). When the reaction is substantially complete, the vinyl amine is isolated and either purified by conventional means, preferably silica gel chromatography, or used directly in the following reaction.

The resultant intermediate amine is a primary or secondary amine (i.e. where at least one of $R^3$ and $R^4$ is hydrogen), and it is protected by dissolving in a tertiary base (preferably pyridine) and reacting with trifluoroacetic anhydride for 5 minutes to 4 hours (preferably 30 minutes) at a temperature of about 25° C. When the reaction is substantially complete, the vinyl trifluoroacetamido compound of Formula 5a is isolated and purified by conventional means, preferably silica gel chromatography.

Alternatively, the intermediate amine where at least one of $R^3$ and $R^4$ is hydrogen is protected by dissolving in an inert solvent in the presence of a tertiary base (preferably triethylamine) and reacting with di t-butyldicarbonate, to form the t-butoxycarbamate derivative.

Preparation of Formula I

As illustrated in Reaction Scheme 1, Step 5, a vinyl amine of Formula 5 or a vinyl trifluoroacetamido compound of Formula 5a is converted to a compound of Formula I by reaction with maleimide.

The vinyl amine of Formula 5 or 5a is dissolved in an aromatic hydrocarbon (preferably toluene) and refluxed with 2–3 molar equivalents (preferably 2 molar equivalents) of maleimide for 6–24 hours (preferably 16 hours). When the reaction is substantially complete, the Diels-Alder adduct is isolated and purified, preferably by silica gel chromatography. This adduct is dissolved in an inert solvent (for example benzene, toluene, methylene chloride, preferably benzene) and treated with 2–3 molar equivalents (preferably 2 molar equivalents) of dichlorodicyanobenzoquinone at a temperature of 20°–50° C. (preferably 25° C.), for 15 minutes to 3 hours (preferably 30 minutes). When the reaction is substantially complete, the resultant carbazole is isolated conventionally. If the starting vinyl amine is of Formula 6a (i.e. if a trifluoroacetate protecting group is present) the carbazole is treated with an inorganic base (sodium hydroxide, potassium hydroxide, and the like, preferably sodium hydroxide) in a protic solvent (for example methanol, ethanol, or a mixture thereof) mixed with tetrahydrofuran for about 15 minutes at about 25° C. in order to cleave the trifluoroacetate protecting group. Alternatively, if the amine is protected with a t-BOC group, the protecting group is removed by treatment with acid. The resulting pyrrolocarbazole of Formula I is isolated and purified, preferably by silica gel chromatography.

Preparation of the Salts of Formula I

The compounds of Formula I can be converted to corresponding acid addition salts. The conversion is accomplished by treatment with a stochiometric amount of an appropriate acid, such as hydrochloric acid (e.g., 3 molar equivalents to form the trihydrochloride salt). Typically, the free base is dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent.

The acid addition salts of the compounds of Formula I can be decomposed to the corresponding free bases by treatment with an excess of a suitable base, such as ammonia or sodium bicarbonate, typically in the presence of an aqueous solvent, and at a temperature between 0° C. and 50° C. The free base form is isolated by conventional means, such as extraction with an organic solvent.

Preferred Compounds

Preferred are the compounds of Formula I where $R^1$ is hydrogen and $R^2$ is 3-thiophenyl. Also preferred are those compounds where $R^3$ is hydrogen and $R^4$ is lower alkyl, more preferably methyl. Further preferred are those compounds which combine the above-mentioned features. Most preferred is the compound:

1,3-dioxo-6-(3-methylaminopropyl)-1,2,3,6-tetrahydro-4-(thiophen-3-yl)-pyrrolo[3,4-c]carbazole.

Utility, Testing and Administration

General Utility

The compounds of the present invention are protein kinase C inhibitors useful as chemotherapeutic agents for treating mammals, particularly humans, having a variety of malignant disease states including: small cell lung carcinoma, colon carcinoma, breast tumors corresponding to MCS7, MDA-MB-435 and MDA-N cell lines, and PKC over expressing tumors, such as those corresponding to CHO/PKC-ε. Different compounds of the invention exhibit greater activity against certain tumors as opposed to others, as can be determined by commonly used methods.

Testing

In vitro activity for protein kinase C inhibition, is quantitated by measuring incorporation of $^3P$ from $\gamma\text{-}^{32}P$ ATP into synthetic peptide substrates.

In vivo activity for chemotherapeutic agents, particularly for treating malignant diseases, is determined by tumor inhibition assays, for example as described by Maneckjee, et al., in *Proc. Natl. Acad. Sci. USA*, Vol 89, 1169–1173 (February 1992). Variations of the assay can be performed, e.g., using HT-29 colon carcinoma cells, SCLC H82 cells, CHO/PKC-β and CHO/PKC-ε cells.

Administration

The compounds of Formula 1 are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.1 to 20.0 mg/kg of body weight, preferably about 0.5 to 10.0 mg/kg of body weight, and most preferably about 1.0 to 5.0 mg/kg of body weight. Thus, for administration to a 70 kg person, the dosage range would be about 7.0 to 1,400 mg per day, preferably about 35.0 to 700 mg per day, and most preferably about 70 to 350 mg per day. The amount of active compound administered will, of course, be dependent on the subject and disease state being treated, the severity of the affliction, the manner and schedule of administration and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, etc., such as multidrug resistance reversing agents.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such ae starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc. A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Compounds of Formula 2

1A. Formula 2 Where $R^1$ is Hydrogen

A solution of 2-N,N-dimethylaminomethylindole (5.4 g) (*Acta. Chim. Acad. Sci. Hung.*, Vol 34, p 439 (1962)) in 40 ml of methanol was mixed with methyl iodide (15 ml) and left for 3 hours. Evaporation of the solvent afforded a glass, to which was added triphenylphosphine (11.6 g) and dimethylformamide (DMF) (100 ml). The mixture was refluxed overnight, then most of the DMF distilled off under reduced pressure, and the residue triturated with benzene (75 ml). The crystals that formed were filtered off, washed with a little benzene, and dried under vacuum, to give indole-2-methyltriphenylphosphonium iodide (10.4 g).

1B. Formula 2, Varying $R^1$

By following the procedure of Example 1A and substituting 2-diethylaminomethylindole by 2-diethylaminomethylindoles substituted with the desired $R^1$ substituent, there are obtained the corresponding compounds of Formula 2 where $R^1$ is methyl, ethyl, n-propyl, isopropyl, n-butyl, tert-butyl, n-pentyl, n-hexyl, and the like, for example:

4-methylindole-2-methyltriphenylphosphonium iodide;
5-ethylindole-2-methyltriphenylphosphonium iodide;

6-n-propylindole-2-methyltriphenylphosphonium iodide; and 7-n-butylindole-2-methyltriphenylphosphonium iodide.

Example 2

Preparation of Compounds of Formula 3

2A. Formula 3 Where $R^1$ is Hydrogen and $R^2$ is Thiophen-3-yl

To a solution of 1.04 g of indole-2-methyltriphenylphosphonium iodide in 60 ml of dimethylsulfoxide was added 175 µl of thiophene-3-carboxaldehyde followed by 250 µl 1,8-diazabicyclo[5.4.0]undec-7-ene. The mixture was stirred under $N_2$ at 40° C. for 1 hour, then at 80° C. for 2 hours, and finally allowed to stir overnight at 20° C. The mixture was poured into water and extracted with diethylether. The organic layer was dried, the solvent removed under reduced pressure, and the residue purified by crystallization from methanol. The yield of 2-[2-(thiophen-3-yl)vinyl]indole was 200 mg (44%).

2B. Formula 3, Varying $R^1$ and $R^2$

By following the procedure of Example 2A and optionally substituting indole-2-methyltriphenylphosphonium iodide with other compounds of Formula 2, prepared for example as in Example 1 above, and optionally substituting thiophene-3-carboxaldehyde with other compounds of formula $R^2$CHO, there are obtained the following compounds of Formula 3:

2-[2-(thiophen-2-yl)vinyl]indole;
2-[2-(furan-3-yl)vinyl]indole;
2-[2-(pyrrol-3-yl)vinyl]indole;
2-[2-(pyrid-3-yl)vinyl]indole;
4-methyl-2-[2-(thiophen-3-yl)vinyl]indole;
5-ethyl-2-[2-(thiophen-3-yl)vinyl]indole;
6-n-propyl-2-[2-(thiophen-3-yl)vinyl]indole; and
7-n-butyl-2-[2-(thiophen-3-yl)vinyl]indole.

Example 3

Preparation of Compounds of Formula 4

3A. Formula 4 Where $R^1$ is Hydrogen and $R^2$ is Thiophen-3-yl

A solution of 2-[2-(thiophen-3-yl)vinyl]indole (200 mg) was dissolved in 3 ml of dimethylformamide and treated with 40 mg of potassium hydride at 25° C. for 15 minutes. 1-Iodo-3-(t-butyldiphenylsilyloxy)propane (500 mg) was then added, and the reaction mixture allowed to stir overnight at 25° C. After partitioning the mixture between diethylether and water, the organic layer was dried, and solvent removed under reduced pressure. The residue was purified by preparative TLC on silica gel (eluting with 5:1 hexane/EtOAc). The yield of 1-[3-(t-butyldiphenylsilyloxy)propyl]-2-[2-(thiophen-3-yl)vinyl]indole was 330 mg (71%).

The material was dissolved in 2 ml of tetrahydrofuran and treated with 2 ml of a solution of 1M tetrabutylammonium fluoride at 25° C. for 2 hours. After partitioning the mixture between diethylether and water, the organic layer was dried, and solvent removed under reduced pressure. The residue was purified by preparative TLC on silica gel (eluting with 2:1 hexane/EtOAc) to obtain 121 mg of 1-(3-hydroxypropyl)-2-[2-(thiophen-3-yl)vinyl]indole (68%).

3B. Formula 4, Varying $R^1$ and $R^2$

By following the procedure of Example 3A, substituting 2-[2-(thiophen-3-yl)vinyl]indole with other compounds of Formula 3, e.g., as prepared in Example 2 above, there are obtained the corresponding hydroxypropyl compounds of Formula 4.

Example 4

Preparation of Compounds of Formula 5a

A. Formula 5a Where $R^1$ is Hydrogen, $R^2$ is Thiophen-3-yl, $R^3$ is Hydrogen, and $R^4$ is Methyl A solution of 1-(3-hydroxypropyl)-2-[2-(thiophen-3-yl)vinyl]indole (121 mg) in 3 ml of methylene chloride was treated with 120 µl of 2,6-lutidine and cooled to 0° C. Trifluoromethanesulfonic anhydride (100 µl) was added, and after stirring for 30 minutes 5 ml of 40% aqueous methylamine was introduced, and the reaction mixture stirred at 25° C. for 3 hours. After stirring for a further 12 hours at 0° C., the reaction mixture was partitioned between methylene chloride and water, the organic layer dried, and solvent was removed under reduced pressure. Preparative TLC on silica gel (eluting with 10% methanol/methylene chloride) gave 83 mg of 1-[3-(methylamino)propyl]-2-[2-(thiophen-3-yl)vinyl]indole (67%). This product was dissolved in 3 ml of methylene chloride containing 150 µl of pyridine and trifluoroacetic anhydride (40 µl) was added. After 30 minutes, the mixture was partitioned between diethylether and aqueous sodium bicarbonate, the organic layer dried, and solvent was removed under reduced pressure. Preparative TLC on silica gel (eluting with 3:1 hexane/EtOAc) gave 80 mg of 1-[3-(N-methyltrifluoromethylacetamido)propyl]-2-[2-(thiophen-3-yl)vinyl]indole (73%).

4B. Formula 5a, Varying $R^1$, $R^2$, $R^3$ and $R^4$

By following the procedure of Example 4A and optionally substituting 1-(3-hydroxypropyl)-2-[2-(thiophen-3-yl)vinyl]indole with the compounds of Formula 4, e.g., as prepared in Example 3 above, there are obtained the corresponding compounds of Formula 5 and 5a.

Example 5

Preparation of Compounds of Formula I

5A. Formula I Where $R^1$ is Hydrogen, $R^2$ is Thiophen-3-yl, $R^3$ is Hydrogen, and $R^4$ is Methyl A solution of 1-[3-(N-methyltrifluoromethylacetamido)propyl]-2-[2-(thiophen-3-yl)vinyl]indole (80 mg) in 2 ml of toluene was treated with 40 mg of maleimide. After refluxing overnight, the solvent was evaporated under reduced pressure, and the residue purified by preparative TLC on silica gel, to give 20 mg of the Diels-Alder adduct (20%).

$^1$H NMR (CDCl$_3$): 7.96 (m, 1H), 7.35–7.15 (m, 4H), 7.13 (m, 1H), 7.02 (m, 1H), 4.40 (d, 1H), 4.13 (t, 2H), 3.73 (m, 2H), 3.45 (t, 2H), 3.12 (m, 2H), 3.06 (s, 3H), 2.02 (5.2H).

This material was dissolved in 3 ml of benzene and treated with 20 mg of dichlorodicyanobenzoquinone (DDQ). After 20 minutes, another 10 mg of DDQ was added. After 10 minutes, the reaction mixture was applied to a preparative TLC plate and eluted with 2:1 hexane/EtOAc. In this manner 18 mg of 1,3-dioxo-6-(N-methyltrifluoromethylacetamido)-1,2,3,6-tetrahydro-4-(thiophen-3-yl)-pyrrolo[3,4-c]carbazole was obtained as a yellow foam.

This product was dissolved in 4 ml of 1:1 MeOH/THF, and 1 ml of 1M NaOH was added. After stirring for 15 minutes, the mixture was partitioned between methylene chloride and water. The organic layer was separated and solvent removed under reduced pressure. Preparative TLC of the residue (eluting with 10% methanol in methylene chloride) gave 15 mg of 1,3-dioxo-6-(3-methylaminopropyl)-1,2,3,6-tetrahydro-4-(thiophen-3-yl)-pyrrolo[3,4-c]carbazole.

$^1$H NMR (d$_6$-DMSO): 8.96 (d, H), 8.00 (s, 1H), 7.95 (m, 1H), 7.74 (d, 1H), 7.62 (m, 3H), 7.35 (t, 1H), 4.59 (t, 2H), 2.55 (t, 2H), 2.29 (s, 3H 1.97 (t, 2H). HRMS calcd. for $C_{22}H_{19}N_3O_2S$: 389.1197; Found: 389.1198.

5B. Formula I, Varying $R^1$, $R^2$ and $R^3$

By following the procedure of Example 5A and substituting 1-[3-(N-methyltrifluoromethylacetamido)propyl]-2-[2-(thiophen-3-yl)vinyl]indole with other compounds of Formula 5 or 5a, prepared for example as in Example 4B above, there are obtained the corresponding pyrrolocarbazole derivatives of Formula I.

Example 6

This example illustrates the preparation of a representative pharmaceutical formulation for oral administration containing an active compound of Formula I, e.g., 1,3-dioxo-6-(3-methylaminopropyl)-1,2,3,6-tetrahydro-4-(thiophen-3-yl)-pyrrolo[3,4-c]carbazole.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–6, can be used as the active compound in the preparation of the orally administrable formulations of this example.

Example 6

This example illustrates the preparation of another representative pharmaceutical formulation for oral administration, containing an active compound of Formula I, e.g., 1,3-dioxo-6-(3-methylaminopropyl)-1,2,3,6-tetrahydro-4-(thiophen-3-yl)-pyrrolo[3,4-c]carbazole.

| Ingredients | Quantity per tablet mgs. |
| --- | --- |
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 1–6, can be used as the active compound in the preparation of the orally administrable formulations of this example.

Example 7

This example illustrates the preparation of a representative pharmaceutical formulation containing an active compound of Formula I, e.g., 1,3-dioxo-6-(3-methylaminopropyl)-1,2,3,6-tetrahydro-4-(thiophen-3-yl)-pyrrolo[3,4-c]carbazole.

An suspension for oral administration is prepared having the following composition:

| Ingredients | Amount |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 1.00 ml |

Other compounds of Formula I, such as those prepared in accordance with Examples 1–6, can be used as the active compound in the preparation of the orally administrable formulations of this example.

Example 8

This example illustrates the preparation of a representative pharmaceutical formulation containing an active compound of Formula I, e.g., 1,3-dioxo-6-(3-methylaminopropyl)-1,2,3,6-tetrahydro-4-(thiophen-3-yl)-pyrrolo[3,4-c]carbazole An injectable preparation buffered to a pH of 7.4 is prepared having the following composition:

| Ingredients | Amount |
| --- | --- |
| Active compound | 0.2 g |
| Sodium Acetate Buffer Solution (0.4 M) | 2.0 ml |
| HCl (1N) | q.s. to pH 7.4 |
| water (distilled, sterile) | q.s. to 20 ml |

Other compounds of Formula I, such as those prepared in accordance with Examples 1–6, can be used as the active compound in the preparation of the injectable formulations of this example.

Example 9

This example illustrates the preparation of a representative pharmaceutical formulation containing an active compound of Formula I, e.g., 1,3-dioxo-6-(3-methylaminopropyl)-1,2,3,6-tetrahydro-4-(thiophen-3-yl)-pyrrolo[3,4-c]carbazole.

A suppository totalling 2.5 grams is prepared having the following composition:

| Active compound | 500 mg |
| --- | --- |
| witepsol H-15* | balance |

(*triglycerides of saturated vegetable fatty acid; a product of Riches-Nelson, Inc., New York, N.Y.).

Other compounds of Formula I, such as those prepared in accordance with Examples 1–6, can be used as the active compound in the preparation of the suppository formulations of this example.

Example 10

In Vitro Determination of Activity Utilizing Protein Kinass C Inhibition Assay

Protein Kinase C (PKC) inhibitory activity is quantitated by measuring incorporation of $^{32}P$ from $\gamma\text{-}^{32}P$ ATP into synthetic peptide substrates. The inhibitory potential is measured using the β1 isozyme of PKC from rat brain and the synthetic peptide substrate ala-lys-arg-arg-arg-leu-ser-ser-leu-arg-ala.

A reaction mixture containing 25 mM Tris-HCl, pH 7.5, 2.5 mM Mg(NO$_3$), 1.0 mM EGTA, 20 µM substrate, 1 µg/mL phosphatidlserine (PS), 5×10$^{-6}$M diacylglycerol(di-C8), and 50 µM ATP is spiked with γ-$^{32}$P ATP (>5,000 Ci/mmol) to provide approximately 10$^6$ CPM per reaction and 0.08 µg/mL PKC in a 50 µl volume per well. The assay is run with or without test compound, added at various concentrations. After five minutes incubation at room temperature, the reaction is stopped by the addition of 0.2V of a 50% TCA solution. A 30 µl sample from each well (control and test compound) is then spotted onto Whatman P-81 ion exchange chromatography paper, and 32-P incorporation is then counted on a Beckman LS 5000 TA liquid scintillation counter. The percent inhibition of PKC activated by 5×10$^{-6}$M diC8 and 1 µg/mL phosphatydil serine is determined according to the formula:

% Inhibition=1.0 -[(sample CPM-basal CPM)/(total CPM-basal CPM)]×100 and the concentration necessary to achieve 50% Inhibition is determined.

The compounds of the present invention are active inhibitors of protein kinase C when tested by this method; for example 1,3-dioxo-6-(3-methylaminopropyl)-1,2,3,6-tetrahydro-4-(thiophen-3-yl)-pyrrolo[3,4-c]carbazole-IC$_{50}$ 30 nM.

Example 11

In Vivo Determination of Activity Utilizing Small Cell Lung Carcinoma Xenograft Assay This procedure is a modification of a procedure described by Maneckjee, et al., in *Proc. Natl. Acad. Sci. USA*, Vol 89, 1169–1173 (Febuary 1992).

H82 small cell lung carcinoma (SCLC) cells are thawed from frozen stock and grown in RPMI. Prior to injection, the cells are trypsinized, counted, and resuspended in PBS:solubilized basement membrane preparation (Matrigel®) (1:2) to concentrations of 5×10$^5$ or 1.5×10$^6$ cells/ml. Female athymic nude mice, 4–5 weeks old (Harlan Sprague Dawley) receive 200 R/mouse irradiation one day prior to challenge, and are given 0.2 ml SCLC/mouse by subcutaneous injection in the flank (concentrations of 1×10$^5$ or 3×10$^5$ SCLC cells/mouse). Groups of 30 mice are treated intraperitoneally, once a day, with test compound at 10 mg/kg (solubilized in DMSO and diluted to final vehicle concentration of 20% DMSO in PBS). Treatments are started 2 hours post-challenge and continue for 45 days. Vehicle treated and untreated mice are used as controls.

Statistical Analysis:

A Fisher Exact test [Kendall M., Stuart A., *The Advanced Theory of Statistics*, Vol., 2 (MacMillan Pub. Co. New York, 1979)] is used to compare tumor occurrence rates between groups. The Mann Whitney U test [Hollander N., Wolfe D. A., *Non-parametric Statistical Methods* (John Wiley and Sons, Inc., New York, 1973)] is used to compare differences in survival time and a log rank test (Kalbfleisch J. D., Prentice R. L., *The Statistical Analysis of Failure Time Data* (John Wiley and Sons, Inc., New York 1980)] is used to compare the time for each tumor to reach 2000 mm$^3$.

Compounds of the present invention inhibit tumor growth when tested by this method.

Example 12

In Vivo Determination of Activity Utilizing Colon Carcinoma Xenograft Assay

By following the procedure of Example 12 and substituting H82 small cell lung carcinoma cells with HT-29 colon cancer cells, grown to a concentration of 5×10$^6$ cells/ml and administered at a concentration of 1×10$^6$ cells/mouse, activity against colon carcinoma is determined.

Compounds of the present invention inhibit tumor growth when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed:

1. A compound represented by the formula:

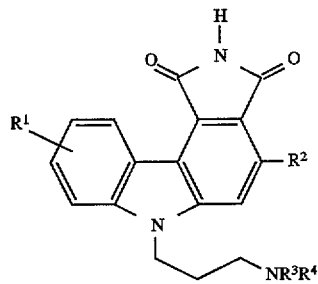

wherein:

R$^1$ is hydrogen or lower alkyl;

R$^2$ is 3-thiophenyl and

R$^3$ and R$^4$ are independently hydrogen or lower alkyl;

or a pharmaceutically acceptable salt thereof.

2. The compound of claim 1, wherein R$^1$ is hydrogen.

3. The compound of claim 2, wherein R$^3$ is hydrogen and R$^4$ is lower alkyl.

4. The compound of claim 3, wherein R$^3$ is hydrogen and R$^4$ is methyl, namely 1,3-dioxo-6-(3-methylaminopropyl)-1,2,3,6-tetrahydro-4-(thiophen-3-yl)-pyrrolo[3,4-c]carbazole.

5. A pharmaceutical composition comprising a compound or salt of claim 1 and a pharmaceutically acceptable excipient.

* * * * *